(12) United States Patent
Schuetze et al.

(10) Patent No.: US 7,651,856 B2
(45) Date of Patent: Jan. 26, 2010

(54) MOUNTING DEVICE FOR MOUNTING A RETAINER MEANS FOR A BIOLOGICAL OBJECT AND CORRESPONDING METHOD FOR LASER MICRO-DISSECTION

(75) Inventors: Raimund Schuetze, Tutzing (DE); Bernd Saegmueller, Weilhelm (DE); Kurt Harms, Bernried (DE); Yilmaz Niyaz, Augsburg (DE)

(73) Assignee: Carl Zeiss MicroImaging GmbH (DE)

( * ) Notice: Subject to any disclaimer, the term of this patent is extended or adjusted under 35 U.S.C. 154(b) by 405 days.

(21) Appl. No.: 10/596,438

(22) PCT Filed: Nov. 11, 2004

(86) PCT No.: PCT/EP2004/012793

§ 371 (c)(1),
(2), (4) Date: Jul. 7, 2006

(87) PCT Pub. No.: WO2005/057178

PCT Pub. Date: Jun. 23, 2005

(65) Prior Publication Data

US 2007/0031816 A1    Feb. 8, 2007

(30) Foreign Application Priority Data

Dec. 15, 2003   (DE)   ................. 103 58 566

(51) Int. Cl.
*C12N 5/00*    (2006.01)
*G01N 1/00*    (2006.01)

(52) U.S. Cl. ........................................ 435/378; 356/36

(58) Field of Classification Search .................. None
See application file for complete search history.

(56) References Cited

U.S. PATENT DOCUMENTS 3,749,369 A * 7/1973 Landsberger ............... 366/273
5,998,129 A   12/1999 Schutze et al.

(Continued)

FOREIGN PATENT DOCUMENTS

DE           38 41 961 A1      6/1990

(Continued)

*Primary Examiner*—Jill Warden
*Assistant Examiner*—Timothy G Kingan
(74) *Attorney, Agent, or Firm*—Mayback & Hoffman, P.A.; Gregory L. Mayback; Scott D. Smiley

(57) ABSTRACT

To enable contactless laser microdissection in a closed container (10, 11), for example in the form of a Petri dish, it is proposed according to the invention to use a holding device which comprises a receiving portion (4) for arrangement in the container (10, 11) and a holding portion (1) for arrangement externally of the container (10, 11). The receiving portion (4) serves to receive at least one receiving means (9), which serves in turn to receive or collect at least one biological specimen obtained by laser microdissection from biological material (15) located in the container (10, 11). The holding portion (1) is coupled to the receiving portion (4) in contactless manner, for example by means of magnetic coupling, in such a way that, by moving the holding portion (1), the receiving portion (4), together with the receiving means (9) held thereby, may be positioned in the closed container (10, 11) precisely over the biological specimen in each case to be received.

9 Claims, 2 Drawing Sheets

U.S. PATENT DOCUMENTS

2003/0180941 A1  9/2003  Schutze

FOREIGN PATENT DOCUMENTS

Figure 3:
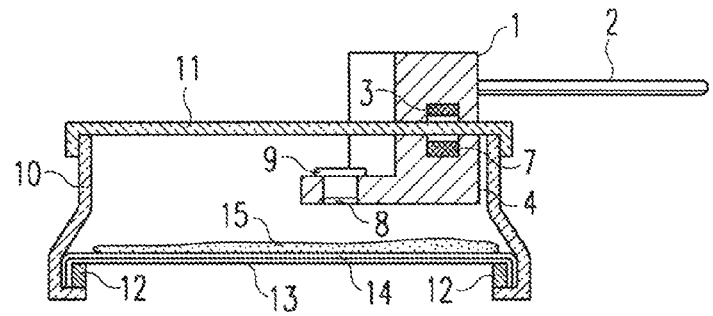

| DE | 198 04 800 | 8/1999 |
| DE | 201 11 939 U1 | 1/2003 |
| WO | WO 97/29355 | 8/1997 |
| WO | WO01/73397 | 10/2001 |
| WO | WO02/14833 | 2/2002 |
| WO | WO 03/008934 | 1/2003 |

* cited by examiner

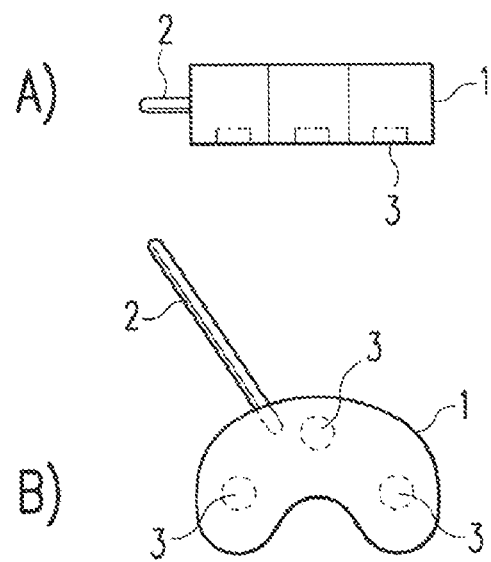
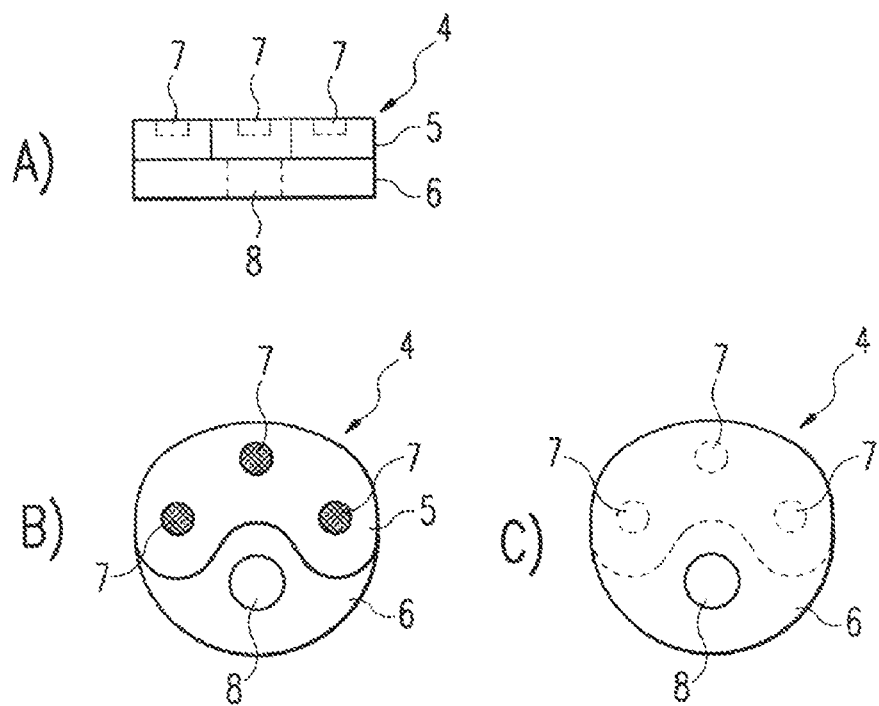

MOUNTING DEVICE FOR MOUNTING A RETAINER MEANS FOR A BIOLOGICAL OBJECT AND CORRESPONDING METHOD FOR LASER MICRO-DISSECTION

The present invention relates to a holding device for holding a receiving means, which is provided for receiving or collecting a biological specimen, in a container, to allow contactless laser microdissection in the container, and to a corresponding method, in particular a laser microdissection method.

A method and a device are known from WO 97/29355 A1 for contactless microinjection and microdissection, i.e. for harvesting and recovering biological specimens from surrounding biological material, by means of laser irradiation. It is proposed in this publication to arrange the biological material to be processed on a carrier film, wherein a previously selected biological specimen is then cut out of the surrounding biological material with the assistance of a laser beam together with a portion of the backing film and transferred by a laser-induced transport process by means of a laser shot onto a collecting substrate arranged immediately above or below, for example in the form of a cap of a microcentrifuge or Eppendorf container (PCR ("Polymerase Chain Reaction") cap). Using this laser microdissection method, it is possible to isolate and sort individual selected biological specimens spatially from a very large number of biological specimens, this in particular proceeding in contactless manner.

As has already been mentioned above, the biological material may be arranged for this purpose on a carrier film or carrier membrane, which is clamped onto a laser light-transmitting glass microscope slide. In the present applicant's WO 02/14833 A1, it was additionally proposed to use a carrier arrangement with holding means for holding and clamping the above-stated carrier membrane, which absorbs laser light, wherein the holding means may be constructed for example in the form of a surrounding frame. In this publication it is likewise proposed to use a carrier arrangement which dispenses with a glass microscope slide and replaces it with an additional, laser light-transmitting membrane, wherein the laser light-absorbing membrane is arranged directly on the laser light-transmitting membrane. The stated carrier arrangement may be incorporated into a container in the form of a Petri dish, in such a way that the two mutually adjacent membranes are clamped in planar manner to the bottom of the main body of the Petri dish. The advantage of this arrangement it that on the one hand live cell cultures may be cultured in the Petri dish and on the other hand biological specimens located in the Petri dish may be subjected directly to the above-described laser microdissection method, in order to isolate the selectable biological specimens from the surrounding biological material without the cell cultures having to be removed from the Petri dish for this purpose and having to be applied to a conventional microscope slide.

Nonetheless, in the above-described arrangement for laser microdissection, the Petri dish needs to be opened in order to be able to transfer the selected biological specimens out of the Petri dish to the desired collecting vessel. This requires not only increased effort but may also result in the most varied kinds of impurities entering the Petri dish and possibly having a negative effect on the biological material located therein. Furthermore, in the above-described procedure it is not possible to work in completely sterile surroundings, since not only does the Petri dish have to be opened for the laser microdissection process but also the collecting vessel with the biological specimen catapulted therein is subsequently held in a non-sterile environment in the respective laser microdissection system.

A microscope slide with a carrier substrate is known from WO 03/008934 A1, wherein mobilising agents are arranged on the side of the carrier substrate remote from a preparation, said mobilising agents being particles which interact with an electromagnetic force. A dissection portion of the carrier substrate is cut out together with the mobilising agents present on the rear face and a preparation portion located on the front by means of laser irradiation and drops into a collecting vessel 10, on the bottom of which there acts a magnetic force means 11 for generating a magnetic force during dissection. The magnetic force means may be a toroidal core magnet or a coil through which current flows. The magnetic force is generated by the magnetic force means in such a way that the dissected material comprising the dissection portion and the preparation portion may be located purposefully on the base of the collecting vessel 10.

A method is furthermore known from DE 198 04 800 A1 for the automatic retrieval of specimens applied in planar manner by means of electrostatic or electromagnetic forces, wherein it is assumed that the membrane provided for dissection has previously been electrically charged or has appropriate magnetic properties.

It is an object of the present invention to provide a holding device for holding a receiving means, provided for receiving a biological specimen, in a closed container, for example a Petri dish of the above-described type, by means of which the above-mentioned disadvantages are avoided and in particular laser microdissection is possible in the particular container under completely sterile conditions. It is a further object of the present invention to provide a corresponding method for holding such a receiving means in such a container and to provide a corresponding method for laser microdissection of biological specimens.

Said object is achieved according to the invention by a holding device having the features of claim 1 and a method having the features of claim 18 and a method for laser microdissection having the features of claim 24. The subclaims in each case define preferred and advantageous embodiments of the present invention.

The holding device according to the invention serves to hold a receiving means, for example in the form of a cap of a microcentrifuge tube, or a plurality of receiving means in a closed container, for example in the form of a Petri dish. The holding device comprises a holding portion to be arranged externally of the container and a collecting portion to be arranged in the container, which collecting portion holds the at least one receiving means for receiving one or more biological specimens within the closed container. The receiving means may in particular take the form of a collecting vessel for collecting a biological specimen obtained by means of laser microdissection from biological material located in the container. The holding portion to be arranged externally of the container and the receiving portion to be arranged in the container are coupled in contactless manner in such a way that the receiving portion is held and may be positioned in the closed container with the assistance of the holding portion.

The contactless coupling between the holding portion and the receiving portion may take the form in particular of a magnetic coupling, wherein other types of contactless coupling, for example using electrostatic charging etc., are possible.

As has already been described, the above-stated container may be a Petri dish, wherein there are clamped to the bottom of the container a laser light-transmitting membrane as supporting membrane and a laser light-absorbing membrane as carrier membrane for the biological material located thereon. In this way, selected biological specimens may be separated from the surrounding biological material directly in the container with the assistance of a suitable laser microdissection system and transported in laser-induced manner to the receiving means held in the container by the receiving portion. It is not necessary to open the container for the laser microdissection process.

The invention makes possible, in particular, the completely sterile harvesting or separation of biological specimens in the stated container. To this end, the receiving portion has merely to be sterilised and arranged under sterile conditions in the container. This may proceed in that a cover for the container is placed on the receiving portion and then the holding portion is arranged on the cover. The entire arrangement may then be arranged on or in the container, such that the receiving portion comes to lie in the container while the holding portion outside the container positions the receiving portion in the container. By moving the holding portion, the receiving means may be positioned in any desired manner in the container.

The receiving portion to be arranged in the container is preferably made from a biologically compatible material, i.e. from a material which does not negatively impair the biological properties of the biological material located in the container. Thus, for example, the receiving portion may be made from polytetrafluoroethylene. The holding portion may also consist of this material. In general, plastics materials are possible for both portions.

To position the holding portion, the latter may be provided with a lever, a rod, an arm or the like, such that a user may simply displace manually the holding portion and the receiving portion coupled therewith. Likewise, computer-assisted positioning of the receiving portion by computer-assisted adjustment of the holding portion is possible in a laser microdissection system.

The present invention is explained in greater detail below with reference to the attached drawings and to preferred exemplary embodiments.

Figure 4:
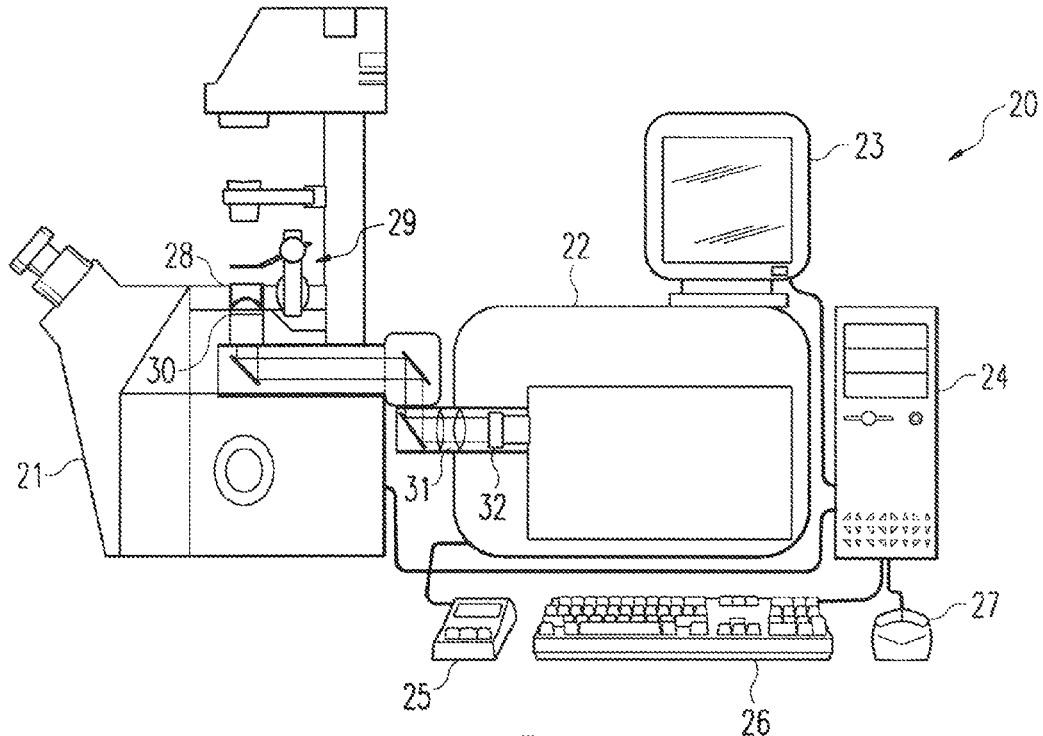

FIGS. 1A and FIG. 1B show a side view or a plan view of a holding portion of a holding device according to a preferred exemplary embodiment of the present invention, FIG. 2A-FIG. 2C show a side view, a plan view from above and a plan view from below of a receiving portion of the holding device according to the invention, FIG. 3 shows a cross-sectional view of a Petri dish with the holding device according to the invention, wherein the holding portion shown in FIG. 1 is arranged externally of the Petri dish and the receiving portion shown in FIG. 2 is arranged in the Petri dish, and FIG. 4 shows a laser microdissection system, in which the present invention may be used.

Before the details of the holding device according to the invention are explained in greater detail, a brief explanation should be given below of the basic principles of laser microdissection with reference to the laser microdissection system illustrated in FIG. 4.

The laser microdissection system 20 shown in FIG. 4 comprises as essential component a laser device 22, in which a laser light source, for example a UV laser, is accommodated for generating a laser beam. Furthermore, a lens system 31 is accommodated in the laser device 22, which system is necessary for coupling the laser beam into a microscope 21 and adjusting the laser focal point in the specimen plane to the optical focal point of the microscope 21. The laser power may be set at an effective level using a neutral filter 32, which is arranged perpendicularly to the laser beam path. The laser beam emitted via an objective 30 impinges on a motorised and computer-controlled microscope or specimen stage 28, on which a carrier carrying biological material to be dealt with may be arranged. Above the specimen stage 28 there is located a manually actuatable or preferably likewise motorised and computer-controlled manipulator 29.

The specimen stage 28 may preferably be moved in the x- and y-directions, while the manipulator 29 may additionally be positioned in the z-direction. A needle or micropipette for microinjection may for example be attached to the manipulator 29. For laser microdissection, the manipulator 29 conventionally holds one or more collecting vessels, wherein the respective collecting vessel needs to be positioned above the laser beam such that biological specimens irradiated with the laser beam may be catapulted by laser irradiation from the specimen stage 28 to the collecting vessel and collected therein.

The microscope 21 may be of any desired design. In particular, it is conceivable to use not only an inverted microscope, as shown in FIG. 4, but also an upright microscope or a laser microscope. The microscope 21 is equipped with a video camera, in particular a CCD ("Charge Coupled Device") video camera, which photographs the area of the specimen stage 28 above the objective 30. The video signal of this video camera is supplied to a conventional commercial computer 24, such that the corresponding video image may be displayed in real time on the screen or monitor 23 of the computer 24. The functions made available by the computer 24 for laser microdissection may be controlled via a keyboard 26 or a computer mouse 27. Furthermore, a foot switch 25 is provided according to FIG. 4, actuation of which allows manual activation of the laser.

The manipulator 29 shown in FIG. 4 is needed for holding collecting vessels, such as for example caps from microcentrifuge containers or microtitre plates etc., if biological specimens are to be conveyed away from the specimen stage 28 to the respective collecting vessel. For the purposes of the present invention, however, the possibility is provided of performing dissection within a closed container, such that for the purposes of the present invention the manipulator 29 is unnecessary per se.

Instead, it is assumed for the purposes of the present invention that a holding device is used for holding the collecting vessel or receiving container which allows the collecting vessel to be held without contact in a closed container. This holding device comprises a holding portion, which is illustrated in FIG. 1A and FIG. 1B in the form of a preferred exemplary embodiment, and a receiving portion for receiving at least one collecting vessel, as illustrated in FIG. 2A-FIG. 2C in the form of a preferred exemplary embodiment.

The holding portion 1 takes the form of a substantially semicircular disk with an indentation. On the bottom of the holding portion 1, a plurality of magnets 3 are arranged in wells. From the side of the holding portion 1 there extends an arm or holder 2, by means of which a user may effect precise positioning of the holding portion 1.

The receiving portion comprises an upper half 5, which is shaped substantially like the holding portion 1. Magnets 7 are arranged in corresponding wells on the top of this upper half 5, which magnets interact with the magnets 3 of the holding portion 1. The lower half 6 of the receiving portion 4 is of substantially circular construction and has a through-hole 8, into which a PCR cap of a microcentrifuge tube may be inserted as collecting vessel.

The above-described holding device serves in separating or harvesting biological specimens, including live cells into the collecting vessel under clean conditions, i.e. under sterile conditions, in a closed container. The holding device is so designed that the sterile receiving portion 4 is held by the non-sterile holding portion 1 in the interior of the respective container in such a way that the hold is firm enough for secure transportation to be ensured during transportation of the container with the holding device. Furthermore, the holding device is so designed that the receiving portion 4 located in the container may be moved with the collecting vessel or the collecting vessels by turning or moving the holding portion 1 from the outside, in order to be able to cover a large proportion of the surface area of the base of the container during a subsequent laser microdissection process, for example for cell harvesting. The transmission of force from the non-sterile holding portion 1 to the sterile receiving portion 3 of the holding device proceeds in contactless manner, i.e. without contact, preferably with the assistance of the magnets 3, 7 shown in FIG. 1 and FIG. 2, wherein it goes without saying that an adequate hold may also be ensured merely by using one magnet in each of the holding portion 1 and the receiving portion 4. Finally, the holding device is also so designed that the receiving portion 4 located in the container with the biological material is biologically compatible or may be rendered biologically compatible, e.g. by sterilisation, autoclaving or such processes. A suitable and biologically compatible material for the receiving portion 4 (and the holding portion 1) is for example polytetrafluoroethylene (PTFE). The material selected in each case and the magnets 7 should preferably be sealed.

The holding device may preferably also be so designed that illumination means (not shown) are incorporated or that the best possible illumination of the sample by the illumination of the corresponding laser microdissection system is possible. This is achieved for the exemplary embodiment illustrated in particular by the indentation for the beam path provided both in the holding portion 1 and in the receiving portion 4, by the shape of the holding device which is open on at least one side and by the fact that the through-hole 8 is not covered and is also clearly visible and accessible from above and from the side.

FIG. 3 shows use of the above-described holding device with a closed container in the form of a Petri dish, which comprises a substantially cylindrical light-transmitting main body 10 and a likewise light-transmitting circular cover 11. The top of the main body 10 is open, while the bottom is covered by a first membrane 13. This membrane 13 may for example likewise consist of polytetrafluoroethylene (trade name Teflon®) and exhibit a thickness of approx. 20-25 µm. The membrane 13 is planar and is clamped to the bottom of the main body 10 between a surrounding circular ring 12 and the main body 10 by means of the ring 12. Arranged directly on this membrane 13, which is laser light-transmitting, is a further membrane 14, which is so designed that it may be cut by means of laser radiation or biological specimens may be catapulted away therefrom using the above-described laser microdissection process. The membrane 14 is consequently made to be laser light-absorbing. The laser light-absorbing membrane 14 and the laser light-transmitting membrane 13 are both clamped between the ring 12 and the main body 10 of the Petri dish in such a way that a planar surface is obtained. The two membranes 13 and 14 may optionally be adhesively bonded to one another or adhere to one another.

Biological material 15 to be processed is applied to the laser light-absorbing membrane 14. The design of the Petri dish according to FIG. 3 is particularly advantageous because cell cultures may be cultured in the Petri dish which may then be subjected directly to laser irradiation for separating individual biological specimens from the biological material 15 without the cell cultures having to be removed from the Petri dish and applied to a conventional microscope slide.

FIG. 3 shows as receiving or collecting vessel 9 a cap of a microcentrifuge tube, which is held in the Petri dish by the receiving portion 4 of the above-described holding device. To arrange this cap 9 in the Petri dish, it is necessary first of all to insert the cap into the sterile receiving portion 4 at a sterile work station. Then the cover 11 of the Petri dish is arranged on the receiving portion 4 with the cap 9 held thereby. Opposite to or in the vicinity of the receiving portion 4, the holding portion 1 is then placed on the cover 11 in such a way that the magnets 3 and 7 of the holding portion 1 and of the receiving portion 4 respectively may bring about magnetic coupling. Then the arrangement formed in this way is positioned on the main body 10 of the Petri dish in such a way that the receiving portion 4 with the cap 9 held thereby is arranged inside the Petri dish, while the holding portion 1 is arranged on the cover 11 externally of the Petri dish. The Petri dish prepared in this way may then be transported or carried by the holding device to a laser microdissection system, for example a laser microdissection system of the type shown in FIG. 4, in order to subject the biological material located inside the Petri dish to a laser microdissection process.

The Petri dish with the biological material located therein must here be positioned above the laser beam of the laser microdissection system in such a way that the laser beam impinges from below on the Petri dish and passes through the laser light-transmitting membrane 13, which serves as base or support for the substantially thinner laser light-absorbing membrane 14. By moving the Petri dish relative to the laser beam, the laser light-absorbing membrane 14 may be cut with the biological material located thereon, in order to cut individual biological specimens which have been selected beforehand out of the surrounding biological material. Once the desired biological specimens have been separated in this way, the biological specimen desired in each case, with the corresponding cut-out portion of the laser light-absorbing membrane 14, may be catapulted upwards into the cap 9 by means of an individual laser shot or individual laser shots, wherein the respective biological specimen remains adhered to the bottom of the cap 9.

As has already been mentioned above, the laser light-absorbing membrane 14 is substantially thinner than the laser light-transmitting membrane 13 serving as support and may for example consist of polyester with a thickness of 0.9 µm-1 µm or polyethylene naphthalene with a thickness of approx. 1.35 µm. A polyethylene naphthalene membrane is advantageous for example for laser treatment of cell tissue, since it is very readily cut with relatively low laser power. On the other hand, a polyester membrane is advantageous if biological specimens lying close together, such as for example chromosomes or filaments, have to be detached from the surrounding biological material 15, since for this purpose selective ablation of the surrounding biological material is often necessary for sample recovery, which is possible with a polyester membrane without destroying the membrane.

The holding device is preferably so designed that, in the event of use in a laser microdissection system, the sample, i.e. the biological material 15, is illuminated as well as possible or the best possible illumination of the sample is ensured. This is ensured in the exemplary embodiment shown in the drawings by the specific shape of the receiving portion 4 and of the holding portion 1. Support may also be provided by using a light-transmitting material for the holding portion 1 and the receiving portion 4.

It goes without saying that the above-described holding device is not limited to holding a cap 9 as collecting vessel and not even merely to holding a collecting vessel. The holding device may also readily be constructed so as to be able to hold a plurality of receiving or collecting vessels. Furthermore, the holding device is also not limited to use in Petri dishes, but rather may be used generally together with closed containers in which there are arranged one or more carriers with biological materials.

A significant advantage of the present invention consists in the fact that laser microdissection of the biological material located in the closed container may be performed completely under sterile conditions, without the container having to be opened for this purpose. By means of the invention, the container may be transported, together with the holding device and the receiving or collecting vessel held thereby in the container, from an appropriate environment or an appropriate work station, for example a sterile biochemical workbench, to a laser microdissection system, it being possible for the container to remain closed during transportation.

In addition, by means of the present invention it is also possible to use a container for handling infectious biological material, for example viruses etc. To this end, containers with membranes extending across them are produced in which one or more microscope slides may be received. A cover or lid is placed thereover, wherein, by means of the holding device according to the invention, one or more collecting vessels may be moved over the laser beam of the corresponding laser microdissection system without the container having to be opened for the purpose of laser microdissection. Equipping the container with the microscope slides or removing them from the container is then preferably performed on a safety workbench, wherein additional sealing of the container for example with an adhesive tape etc. may be advisable during working with the laser microdissection system or during working with a microscope.

Finally, it should be pointed out that the above-described holding device may also be combined with a computer-controlled laser microdissection system in such a way that the holding portion 1 of the holding device or the arm 2 attached thereto is automatically positioned through computer control by the laser microdissection system, in order for example to convey biological specimens which have been selected in computer-assisted manner from the biological material 15 located in the container successively into collecting vessels 9, likewise selected beforehand, which are held by the holding device in the container. To this end, corresponding coupling may be provided between the arm 2 of the holding portion 1 and the manipulator 29, shown in FIG. 4, of the corresponding laser microdissection system, such that the previously selected collecting vessels 9 may be moved in succession over the desired biological specimens of the biological material 15. On the other hand, the relative motion necessary for laser microdissection between the biological material 15 and the laser beam of the laser device 20 takes place via the specimen stage 28 of the laser microdissection system, such that the desired biological specimens of the biological material 15 are moved in succession over the laser beam of the laser device 22.

The holding device according to the invention is suitable not only for laser microdissection, but also in general for holding a receiving means for a biological specimen in a container, in order for example to carry out observation, investigation, processing or the like of the biological specimen located in the particular receiving means using a microscope system.

The invention claimed is:

1. A method for laser microdissection in a container, comprising the steps of:

arranging a receiving portion, holding at least one receiving element, in the container, arranging a holding portion externally of the container, positioning the receiving portion in the container by means of contactless coupling between the holding portion and the receiving portion by moving the holding portion in a direction relative to the container;

holding in the container at least one receiving element for receiving a biological specimen detached by means of laser microdissection from biological material located in the container;

detaching at least one biological specimen by laser microdissection from the biological material located in the container; and receiving the at least one biological specimen by the at least one receiving element held in the container, wherein the receiving portion is held in the container by the holding portion by means of the contactless coupling.

2. A method according to claim 1, wherein in the step of arranging the holding portion, the holding portion is arranged externally of the container in the vicinity of the receiving portion located in the container.

3. A method according to claim 1, wherein in the step of arranging the receiving portion, the receiving portion is arranged on the inside of a cover of the container, and in the step of arranging the holding portion, the holding portion is arranged on the outside of the cover.

4. A method according to claim 3, wherein, after arrangement of the receiving portion on the inside of the cover and of the holding portions on the outside of the cover, the arrangement consisting of the holding portion, the cover and the receiving portion is combined in such a way with a main body of the container that the cover covers the main body and the receiving portion on the inside of the cover is arranged inside the container formed by the main body and the cover.

5. A method according to claim 1, wherein the receiving portion is sterilized before the step of arranging the receiving portion is performed.

6. A method according to claim 1 wherein the holding portion and the receiving portion form a holding device wherein the receiving portion defines at least one hole sized to hold the at least one receiving element and serve as a collecting vessel for collecting a biological specimen recovered using laser microdissection from biological material to be disposed in the container and wherein the holding portion and the receiving portion are coupled in a contactless manner in such a way that the receiving portion is held in the container via the holding portion and the at least one hole of the receiving portion with the at least one receiving element may be positioned at multiple locations within the container by moving the holding portion.

7. A method according to claim 6, wherein, to perform the method, the holding device is used to hold the at least one receiving element in the container.

8. A method according to claim 1, wherein the method is performed in computer-assisted manner.

9. A method according to claim 1 wherein, to perform laser microdissection, a combination of a closed container and a holding device that includes the holding portion and the receiving portion, wherein the receiving portion defines at least one hole sized to hold the at least one receiving element and serve as a collecting vessel for collecting a biological specimen recovered using laser microdissection from biological material to be disposed in the container and wherein the holding portion and the receiving portion are coupled in a contactless manner in such a way that the receiving portion is held in the container via the holding portion and the at least one hole of the receiving portion with the at least one receiving element may be positioned at multiple locations within the container by moving the holding portion is used.

* * * * *